US008986725B2

(12) United States Patent
Stabler et al.

(10) Patent No.: US 8,986,725 B2
(45) Date of Patent: Mar. 24, 2015

(54) SILICONE-PEROXIDE COMPOSITIONS FOR LONG-TERM, CONTROLLED OXYGEN RELEASE

(75) Inventors: Cherie L. Stabler, Coral Gables, FL (US); Benjamin S. Harrison, Tobaccoville, NC (US); Christopher A. Fraker, Hollywood, FL (US); Eileen Pedraza, Coral Gables, FL (US); Camillo Ricordi, Miami, FL (US)

(73) Assignees: University of Miami, Miami, FL (US); Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 13/264,140

(22) PCT Filed: Apr. 15, 2010

(86) PCT No.: PCT/US2010/031232
§ 371 (c)(1),
(2), (4) Date: Dec. 21, 2011

(87) PCT Pub. No.: WO2010/121024
PCT Pub. Date: Oct. 21, 2010

(65) Prior Publication Data
US 2012/0114729 A1 May 10, 2012

Related U.S. Application Data

(60) Provisional application No. 61/169,460, filed on Apr. 15, 2009.

(51) Int. Cl.
*A61K 33/00* (2006.01)
*A61P 41/00* (2006.01)
*A61K 9/00* (2006.01)
*A61L 15/44* (2006.01)
*A61L 15/18* (2006.01)
*A61L 27/54* (2006.01)

(52) U.S. Cl.
CPC ............... *A61L 15/44* (2013.01); *A61L 15/18* (2013.01); *A61L 27/54* (2013.01); *A61L 2300/11* (2013.01); *A61L 2300/602* (2013.01); *A61L 2300/63* (2013.01)
USPC ........................... 424/423; 424/613; 435/375

(58) Field of Classification Search
None
See application file for complete search history.

(56) References Cited

U.S. PATENT DOCUMENTS

| | | |
|---|---|---|
| 4,969,881 A | 11/1990 | Viesturs |
| 5,792,090 A | 8/1998 | Ladin |
| 5,855,570 A | 1/1999 | Scherson et al. |
| 6,000,403 A | 12/1999 | Cantwell |
| 6,368,592 B1 | 4/2002 | Colton et al. |
| 6,767,342 B1 | 7/2004 | Cantwell |

(Continued)

OTHER PUBLICATIONS

Tandara et al. World J Surgery, 2004, 28, 294-300.*

(Continued)

*Primary Examiner* — Kyle Purdy
(74) *Attorney, Agent, or Firm* — Alston & Bird LLP (57) ABSTRACT

A composite for delivering extended-release of oxygen is disclosed. The composite can include a biocompatible polymeric support having a plurality of solid peroxide particles suspended therein. The polymer support can exhibit an oxygen tension value of at least 40 mmHg for a period of 14 days. The weight ratio of biocompatible polymeric support to solid peroxide particles can range from 1:1 to 99:1. Also disclosed is a method of using the composite to deliver oxygen to cells in both in vivo and in vitro environments.

19 Claims, 4 Drawing Sheets

(56) References Cited

U.S. PATENT DOCUMENTS

| | | |
|---|---|---|
| 7,014,630 B2 | 3/2006 | Rosati |
| 7,105,151 B2 | 9/2006 | Unger et al. |
| 2003/0224054 A1 | 12/2003 | Gibbins et al. |
| 2007/0041935 A1* | 2/2007 | Salamone et al. ......... 424/78.27 |
| 2009/0202617 A1* | 8/2009 | Ward et al. .................... 424/447 |
| 2010/0112087 A1* | 5/2010 | Harrison et al. .............. 424/615 |

OTHER PUBLICATIONS

International Search Report and Written Opinion issued in International Application No. PCT/US10/31232 dated Jan. 18, 2011 (11 pages).

Anglin, E. J. et al. Porous silicon in drug delivery devices and materials, Adv. Drug Delivery Rev. 60(11) 1266-1277 (2008).

* cited by examiner

SILICONE-PEROXIDE COMPOSITIONS FOR LONG-TERM, CONTROLLED OXYGEN RELEASE

CROSS REFERENCE TO RELATED APPLICATIONS

This application is a §371 national phase entry of International Application No. PCT/US2010/31232, filed Apr. 15, 2010, which claims priority to U.S. Provisional Patent Application No. 61/169,460, filed Apr. 15, 2009, the entire contents of which are incorporated herein by reference.

FIELD OF THE INVENTION

The present invention is related to silicone-peroxide compositions for controlled release of oxygen, particularly, for controlled release of oxygen when exposed to biological fluids.

BACKGROUND OF THE INVENTION

Various strategies have been developed for generating oxygen in situ. The most common application is in wound healing, where oxygen has been generated via several methods from chemical to electrochemical to thermal et al.

There are simple oxygen reservoirs, which are limited in scope and duration due to the difficulty in implanting tanks that hold enough oxygen to sustain tissues longer than a few hours (U.S. Pat. Nos. 6,000,403; 7,014,630; 4,969,881).

Electrochemical generation of oxygen has been patented for several applications, from wound healing (U.S. Pat. No. 5,855,570) to islet transplantation (U.S. Pat. No. 6,368,592). This method is complicated by the electronics required to generate oxygen. This limits the ability to implant the device and the longevity of oxygen generation. Both of these devices were patented in the 1990s, translation of this technology has proven difficult.

Several patents apply to the use of peroxide in materials (U.S. Pat. Nos. 5,792,090; 6,767,342). Most use hydrogels or degradable materials, which lack the capacity to fully modulate oxygen release from short-term bursts to long-term, tempered release. Furthermore, most applications are for wound healing (U.S. Pat. Nos. 5,792,090; 6,767,342) and not for extending applications where oxygen release must be sustained for a period of a week or more.

SUMMARY OF THE INVENTION

In view of the foregoing background, it is therefore a feature of the present invention to provide a composite for delivering extended-release of oxygen in an aqueous environment. The composite can include a biocompatible polymeric support having a plurality of solid peroxide particles suspended therein. The composite can exhibit an oxygen tension value of at least 40 mmHg for a period of 14 days. A weight ratio of the biocompatible polymeric support to the solid peroxide particles can range from 1:1 to 99:1. The composite can include a platinum catalyst to catalyze cross-linking of the biocompatible polymer support.

The biocompatible polymeric support can include a polymer selected from the group consisting of silicone, polyolefins, polyesters, polystyrene, co-polymers thereof, and mixtures thereof. The biocompatible polymeric support can include a siloxysilane-containing polymer. The siloxysilane-containing polymer can include a vinyl-containing siloxysilane. The siloxysilane-containing polymer can be formed from a polymer precursor comprising a vinyl-containing, alkyl- or alkylaryl-siloxysilane. The polymer precursor can be selected from one or more of the group consisting of:
 3-methacryloyloxypropyltris(trimethylsiloxy)silane,
 3-methacryloyloxypropylpentamethyldisiloxane,
 3-methacryloyloxypropylbis(trimethylsiloxy)methylsilane,
 3-methacryloyloxypropyltris(vinyldimethylsiloxy)silane,
 3-methacryloyloxymethylbis(trimethylsiloxy)(pentamethyldisiloxanyl)silane,
 3-methacryloyloxyethyltris(pentamethyldisiloxanyl)silane,
 methacryloyloxymethylbis(trimethylsiloxy)methylsilane,
 methacryloyloxymethyltris(trimethylsiloxy)silane,
 3-methacryloyloxypropylheptacyclopentyl-T8-silsesquioxane,
 3-methacryloyloxypropylheptaisobutyl-T8-silsesquioxane,
 3-acryloyloxypropylmethylbis(trimethylsiloxy)silane,
 3-acryloyloxypropyltris(trimethylsiloxy)silane,
 3-methacryloyloxypropyl-1,1,1-triphenyl-3,3-dimethyldisiloxane,
 3-methacrylamidopropyltris(trimethylsiloxy)silane,
 3-acrylamidopropyltris(trimethylsiloxy)silane,
 p-vinylphenyltris(trimethylsiloxy)silane,
 p-vinylbenzyltris(trimethylsiloxy)silane,
 vinyloxyethyltris(trimethylsiloxy)silane,
 vinylnonyldimethyl(trimethylsiloxy)silane,
 vinylnonyltris(trimethylsiloxy)silane,
 vinylmethylbis(trimethylsiloxy)silane,
 vinylpentamethyldisiloxane,
 O-(vinyloxyethyl)-N-(tris[trimethylsiloxy]silylpropyl) urethane,
 vinylphenylbis(trimethylsiloxy)silane,
 vinyltris(dimethylsiloxy)silane,
 vinyltris(trimethylsiloxy)silane,
 vinyl-terminated polydimethylsiloxane,
 polydimethylsiloxane monoacrylate,
 polydimethylsiloxane monomethacrylate,
 polymethylphenylsiloxane monoacrylate,
 polymethylphenylsiloxane monomethacrylate, and
 3-acryloyloxypropyltris(polydimethylsiloxanyl)silane.

The siloxysilane-containing polymer can be formed from at least one polymer precursor selected from the group consisting of: vinyl-terminated polydimethylsiloxane, polydimethylsiloxane monoacrylate, and polydimethylsiloxane monomethacrylate The solid peroxide particles can include a peroxide selected from the group consisting of calcium peroxide, sodium peroxide, magnesium peroxide, and combinations thereof. The composite can include cellular material coupled to the biocompatible polymeric support.

The invention also includes a method of making the composite for delivering extended-release of oxygen. The method can include mixing an anhydrous polymer precursor solution and a plurality of solid peroxide particles until the plurality of solid peroxide particles are suspended in the polymer precursor solution. The anhydrous monomer solution can then be cured with a biocompatible catalyst. The biocompatible catalyst can be platinum. The biocompatible catalyst can be added to the anhydrous polymer precursor solution prior to the mixing step.

In another embodiment, the invention includes a method of delivering oxygen to cells. The method can include introducing a composite for delivering extended-release of oxygen in an aqueous fluid, wherein the composite is in fluid communication with a plurality of cells. The introducing step can be in vitro or in vivo.

These and other embodiments are described in more detail below.

BRIEF DESCRIPTION OF THE DRAWINGS

There are shown in the drawings, embodiments which are presently preferred. It is expressly noted, however, that the invention is not limited to the precise arrangements and instrumentalities shown in the drawings.

DETAILED DESCRIPTION

The present invention is directed to a composite for providing extended-release of oxygen in an aqueous environment, a method of making the same, and a method of using the same. The composites can be used in vitro for cell and tissue cultures or in vivo as part of a surgical procedure, wound healing device, regeneration, or cellular transplant In one embodiment, the composite for delivering extended-release of oxygen can include a biocompatible polymeric support having a plurality of solid peroxide particles suspended therein. The weight ratio of biocompatible polymeric support to solid peroxide particles in the composite can range from 1:1 to 99:1. The weight ratio of the biocompatible polymeric support to solid peroxide particles can range from 1:1 to 50:1, from 1:1 to 25:1, from 1.5:1 to 15:1, or any combination thereof (e.g., 1.5:1 to 50:1).

The inventive oxygen-releasing composites can maintain an oxygen tension value of 60 mmHg or greater for 7 days and an oxygen tension value of at least 40 mmHg for 14 days. The oxygen tension can be between 60 and 160 mmHg for 7 days, or 70 mmHg or greater, or 80 mmHg or greater of 90 mm or greater for 7 days. The oxygen tension value can be at least 40 mmHg for 14 days, at least 50 mmHg for 14 days, at least 60 mmHg for 14 days, at least 70 mmHg for 14 days, or at least 80 mmHg for 14 days. The oxygen tension value can be at least at least 40 mmHg for 21 days, at least 50 mmHg for 21 days, or at least 60 mmHg for 21 days.

As used herein, an "oxygen tension value" is the oxygen tension present in a saline buffer at a given time after an inventive oxygen-releasing composite is placed in the saline buffer using the method described below. Oxygen tension values measured herein are reported using either mmHg of $O_2$, i.e., partial pressure, or as a percentage of atmospheric pressure, i.e., $100\% \times [\text{mmHg of } O_2]/[760 \text{ mmHg}]$. In the test method, the inventive oxygen-releasing composite is placed in an incubator, e.g., a cuvette, filled with buffered saline equilibrated to have a starting oxygen tension of 35 mmHg. A solid disk of the oxygen-releasing composite 10 mm in diameter and 1 mm in thickness is placed in 1 mL of buffered saline having an equilibrated oxygen tension of 35 mmHg immediately prior to commencing the test. The oxygen tension in the cuvette is then monitored using an oxygen sensing system. For example, a noninvasive oxygen monitoring system sold under the PreSens trademark. The oxygen-releasing composite is spatially separated from the oxygen sensor within the saline bath to avoid artificially high oxygen tension readings. When the oxygen-releasing composites are porous, or particles, or other non-solid forms, the test should be conducted maintaining the composite-to-saline-buffer volume ratio of 0.0785:1 used with the disks described above.

The biocompatible polymeric support can include a variety of components that can include, but are not limited to, polymers, fillers, antimicrobials, antioxidants, free radical scavengers, adhesion promoters, growth promoters, pharmaceuticals, nutraceuticals, additional active ingredients and adjuncts. Exemplary free radical scavengers include, but are not limited to, cerium oxide, cerium oxide nanoparticles, SOD catalase, and other catalase. The biocompatible polymeric support can include a polymer. The polymer can be hydrophobic or amphiphilic.

The solid peroxide particles can include a peroxide selected from the group consisting of calcium peroxide, sodium peroxide, magnesium peroxide, lithium peroxide, potassium peroxide, and combinations thereof. The solid peroxide particles can have an average particle size ranging from 1 nm to 750 μm, or from 50 nm to 500 μm, or from 500 nm to 400 μm, or from 10 μm to 300 μm.

It has been discovered that low diffusivity polymers, including hydrophobic or amphiphilic polymers, are useful to provide safe, extended-release of oxygen. It is believed this is related to the delayed reaction between the solid peroxide and water, which generates the oxygen. Example of the oxygen generating reaction include the reaction of sodium peroxide with water, which produces sodium hydroxide and hydrogen peroxide according to the following formula:

$$Na_2O_2 + 2\ H_2O \rightarrow 2\ NaOH + H_2O_2$$

The hydrogen peroxide spontaneously decomposes into water and oxygen according to the following formula:

$$2\ H_2O_2 \rightarrow 2\ H_2O + O_2$$

The intermediate product, hydrogen peroxide ($H_2O_2$) is one of the most powerful oxidizers known and can be dangerous when directly contacted with biological material, such as cells, skin, organs or other tissues. It has unexpectedly been discovered that aside from extended release of oxygen, the low diffusivity biocompatible polymeric supports used in the composites disclosed herein prevents the hydrogen peroxide intermediate from diffusing out, and coming in contact with, and potentially damaging, biological materials surrounding the composite.

The biocompatible polymeric support can include a polymer selected from the group consisting of silicones, polyolefins, polyesters, polystyrene, co-polymers thereof, and mixtures thereof. The biocompatible polymeric support can include a siloxysilane-containing polymer.

The siloxysilane-containing polymer can include a vinyl-containing siloxysilane. Similarly, the siloxysilane-containing polymer can be formed from at least one polymer precursor comprising a vinyl-containing, alkyl- or alkylaryl-siloxysilane. The at least one polymer precursor can comprise at least one vinyl-containing, alylk- or alkylaryl-siloxysilane monomer or polymer selected from the group consisting of:
  3-methacryloyloxypropyltris(trimethylsiloxy)silane,
  3-methacryloyloxypropylpentamethyldisiloxane,
  3-methacryloyloxypropylbis(trimethylsiloxy)methylsilane,
  3-methacryloyloxypropyltris(vinyldimethylsiloxy)silane, 3-methacryloyloxymethylbis(trimethylsiloxy)(pentamethyldisiloxanyl)silane,
3-methacryloyloxyethyltris(pentamethyldisiloxanyl)silane,
methacryloyloxymethylbis(trimethylsiloxy)methylsilane,
methacryloyloxymethyltris(trimethylsiloxy)silane,
3-methacryloyloxypropylheptacyclopentyl-T8-silsesquioxane,
3-methacryloyloxypropylheptaisobutyl-T8-silsesquioxane,
3-acryloyloxypropylmethylbis(trimethylsiloxy)silane,
3-acryloyloxypropyltris(trimethylsiloxy)silane,
3-methacryloyloxypropyl-1,1,1-triphenyl-3,3-dimethyldisiloxane,
3-methacrylamidopropyltris(trimethylsiloxy)silane,
3-acrylamidopropyltris(trimethylsiloxy)silane,
p-vinylphenyltris(trimethylsiloxy)silane,
p-vinylbenzyltris(trimethylsiloxy)silane,
vinyloxyethyltris(trimethylsiloxy)silane,
vinylnonyldimethyl(trimethylsiloxy)silane,
vinylnonyltris(trimethylsiloxy)silane,
vinylmethylbis(trimethylsiloxy)silane,
vinylpentamethyldisiloxane,
O-(vinyloxyethyl)-N-(tris[trimethylsiloxy]silylpropyl) urethane,
vinylphenylbis(trimethylsiloxy)silane,
vinyltris(dimethylsiloxy)silane,
vinyltris(trimethylsiloxy)silane,
vinyl-terminated polydimethylsiloxane,
polydimethylsiloxane monoacrylate,
polydimethylsiloxane monomethacrylate,
polymethylphenylsiloxane monoacrylate,
polymethylphenylsiloxane monomethacrylate,
3-acryloyloxypropyltris(polydimethylsiloxanyl)silane,
and a combination thereof.

The siloxysilane-containing polymer can be formed from at least one polymer precursor selected from the group consisting of vinyl-terminated polydimethylsiloxane, polydimethylsiloxane monoacrylate, polydimethylsiloxane monomethacrylate, and mixtures thereof. As used herein, "polymer precursor" can include monomers, oligomers, and polymers that are further polymerized or cross-linked during the formation of the solid peroxide particle-containing composites. The composite can include a catalyst, such as a platinum catalyst, in an amount sufficient to cross-link the polymer precursor.

The composite can, but does not necessarily, include a cellular material coupled to the biocompatible polymeric support. As used herein, "coupled" is used to describe cellular material that is embedded or encapsulated in the biocompatible polymeric support and cellular material that is adhered to the surface of the biocompatible polymeric support. For example, the composite can be a thin coating encapsulating a cellular material, such as a film coating an islet, or the cellular material can be adhered to a surface of the biocompatible polymeric support.

The polymer support can have a diffusion coefficient ranging from $1 \times 10^{-7}$ to $1 \times 10^{-5}$ cm$^2$/sec. The polymer support system can have a diffusion coefficient ranging from $1 \times 10^{-7}$ to $1 \times 10^{-6}$ cm$^2$/sec or from $1 \times 10^{-6}$ to $1 \times 10^{-5}$ cm$^2$/sec.

The diffusion coefficient values reported herein can be determined using a Fourier transform infrared (FT-IR) spectrometry technique. In the method, the polymer is placed between the ATR crystal and the liquid of interest (in sufficient volume to provide a constant concentration). The integrated absorbance of the detected peak of interest is plotted over time. The diffusion coefficient is calculated by curve fitting the data to an equation derived from Fick's second law, which is:

$$\frac{\partial \phi}{\partial t} = D \nabla^2 \phi$$

where:
$\phi$ is the concentration in dimensions of (mol)/cm$^{-3}$;
t is time in seconds; and D is the diffusion coefficient in dimensions of cm$^2$/sec.

An example of this FTIR technique is described in Wurster, D. E., "The Determination of Diffusion Coefficients in Semi-solids by Fourier Transform Infrared (FT-IR) Spectroscopy," 1993.

The polymer support can be a solid material, e.g., a disk or other cut or molded shape, or a micro-/macro-porous scaffold. In some embodiments, the polymer support could be a porous scaffold to enable the loading of cells into the polymer support and promote implant integration into the host. Such an embodiment would enhance the ability of the cells and vasculature from the host to infiltrate into the polymer support.

In other embodiments, the composite for providing extended release of oxygen can be a plurality of microparticles. The microparticle composites can be incorporated into other biomaterials. For example, the peroxide containing composite microparticles can be embedded in fibrin.

The invention also includes a method of making the oxygen-delivering composite for providing extended-release of oxygen over a period greater than one week or greater than two weeks. The method can include mixing an anhydrous polymer precursor solution and a plurality of solid peroxide particles until the plurality of solid peroxide particles are suspended in the anhydrous polymer precursor solution. The method can include curing the hydrophobic polymer precursor solution with a biocompatible catalyst, with heat, or both. The biocompatible catalyst can include platinum. The biocompatible catalyst can be added to the hydrophobic polymer precursor solution prior to the mixing step.

As used herein, "anhydrous polymer precursor solution" refers to a solution having little or no water in order to avoid premature release of oxygen via a reaction between the solid peroxide and water. In general, the "anhydrous polymer precursor solution" will include less than 1 wt-% water, preferably, less than 0.5 wt-%, or less than 0.1 wt-% or less than 0.05 wt-%.

In another embodiment, the invention also includes a method of delivering oxygen to cells. The method can include introducing a composite for delivering extended-release of oxygen into an aqueous fluid. The composite can be in fluid communication with a plurality of cells to which the oxygen is delivered. As used herein, the phrase "aqueous fluid" is intended to include any water-containing fluid including, but not limited to, bodily fluids and culture media.

The method of delivering oxygen to cells can include using the inventive composites for delivering oxygen generating material to cells in a closed-loop bioreactor. Currently, such bioreactors receive oxygen from oxygen bubblers within the system. However, using the inventive composites enable a truly closed system. This simplifies the process of maintaining a sterile environment within the closed-loop bioreactor.

The introducing step can be an in vitro introducing step or an in vivo introducing step. In some embodiments, the composite can be implanted during a surgical procedure in order to enhance cell viability while vessels are regenerating to provide blood flow and oxygen to damaged or implanted tissue.

During the last several decades, the use of agents or components with the capacity to generate oxygen in situ has been investigated. Transplantation of cells and tissues in vivo are commonly met with the problem of oxygen hypoxia, which quickly leads to cell dysfunction and death. While access to a fully developed vascular bed assists in providing the proper level of oxygen, it is rare that implants are placed in areas where this access is immediately feasible. Intravascular transplantation of cells can provide this high level of nutrient delivery; however, direct interaction between cells and blood commonly leads to complications of clot formation and inflammatory instigation. In order to immediately meet the inherent need of cells for access to adequate oxygenation, several groups have attempted to utilize various oxygen generating agents, from algae, oxygen tanks, electrochemical generators, and peroxide. These methods could provide a bridge to providing adequate oxygenation to the cells until a fully developed and functional vascular network is created.

The composites disclosed herein address this need through the use of solid peroxide. Solid peroxide has a high reactivity to water with hydrogen Sand oxygen as end products. This process commonly is highly efficient, where a 1% vol/vol solution of peroxide and water will result in complete degradation of the peroxide within a few hours. The novel composites described herein, however, moderate the reactivity of peroxide by coating the peroxide with a highly stable, low-diffusivity, hydrophobic material. The stability of the coating material allows for long-term modulation of the encased peroxide, without the concern of degradation. Hydrophobicity of the material is key as well, given that the hydrophobic nature of the material provides for reduced diffusivity, which delays (but does not stop) the ability of water to react with the embedded peroxide. The following data shows a significant enhancement in the long-term generation of oxygen through the use of a low diffusivity material, e.g., silicone. In addition, the data has unexpectedly shown a significant decrease in free-radical generation effects and hydrogen peroxide release when incorporated in the low diffusivity material. While prior art peroxide/hydrogel composites resulted in significant cell death, particularly to beta cells, this inventive peroxide/low diffusivity materials, e.g., silicone, do not exhibit this deficiency.

Through the use of a peroxide/low diffusivity composite, the inventors have created a material with the capacity to release a sustained and appropriate level of oxygen over the course of several weeks. Co-implantation of this peroxide/silicone material with cells allows the cells to be exposed to adequate oxygen levels in vivo, allowing time for blood vessels to grow and reach the tissue.

EXAMPLES

The oxygen releasing material was fabricated from non-degradable, hydrophobic materials, such as silicone, incorporated with a solid peroxide powder, i.e., calcium peroxide. The percent loading of the peroxide within the material and the geometry and dimensions of the final scaffold determine the overall release rates and longevity of oxygen release. The release of oxygen can be for at least 21 days. The release of oxygen is modulated by the diffusion of water into the hydrophobic material and the reaction of the peroxide with the water, forming by-products of hydrogen and oxygen. The use of a low diffusion material, generally a hydrophobic material, dramatically changes the characteristics of oxygen release, from a strong burst of oxygen over the course of 24 to 72 hours, to a moderate and sustained release of oxygen over the course of 14 to 45 days.

Materials

The hydrophobic material used for these studies was polydimethylsiloxane (PDMS), a medical grade silicone, cured via platinum catalyst. The peroxide powder was calcium peroxide.

Synthesis of Silicone/Peroxide Materials

The silicone itself is comprised of a PDMS bi-component system comprising: Part A: a polydimethylsiloxane comprising platinum, and Part B: a vinylpolydimethylsiloxane modified silica. An exemplary PDMS bi-component silicone is sold as GE Silicone TRV 615 by the GE Silicones. The volume ratio of Part A to Part B for the examples disclosed herein was 4:1. The desired volumes of PDMS polymer and platinum catalyst are measured out using a plunger pipette since they are both highly viscous. The desired mass of calcium peroxide powder was weighed out to produce composites with a silicone to calcium peroxide weight ratio of 3:1 (w/w).

The PDMS (Part B) was dispensed into a medium-sized plastic petri dish. Platinum catalyst (Part A) was added to the PDMS and they were blended together evenly using a spatula. While still constantly stirring, calcium peroxide was slowly added to the PDMS:platinum mixture. Once all of the calcium peroxide powder was dispersed, the homogenous mixture was placed under vacuum for 1 hour to remove any air bubbles introduced by the mixing. The mixture was then removed from the vacuum and placed in a drying oven set at 40° C. for at least one hour to cure the silicone. To obtain the final product, a cork borer was used to cut out disks of the desired dimensions from the cured 25 wt-% peroxide/75 wt-% silicone material. For in vitro incubation with cells, the 25 wt-% peroxide/75 wt-% silicone disks are submerged in aqueous media for 30 minutes prior to use in order to avoid the initial rise in the release of oxygen.

Characterization of Silicone/Peroxide Materials

Figure 1:
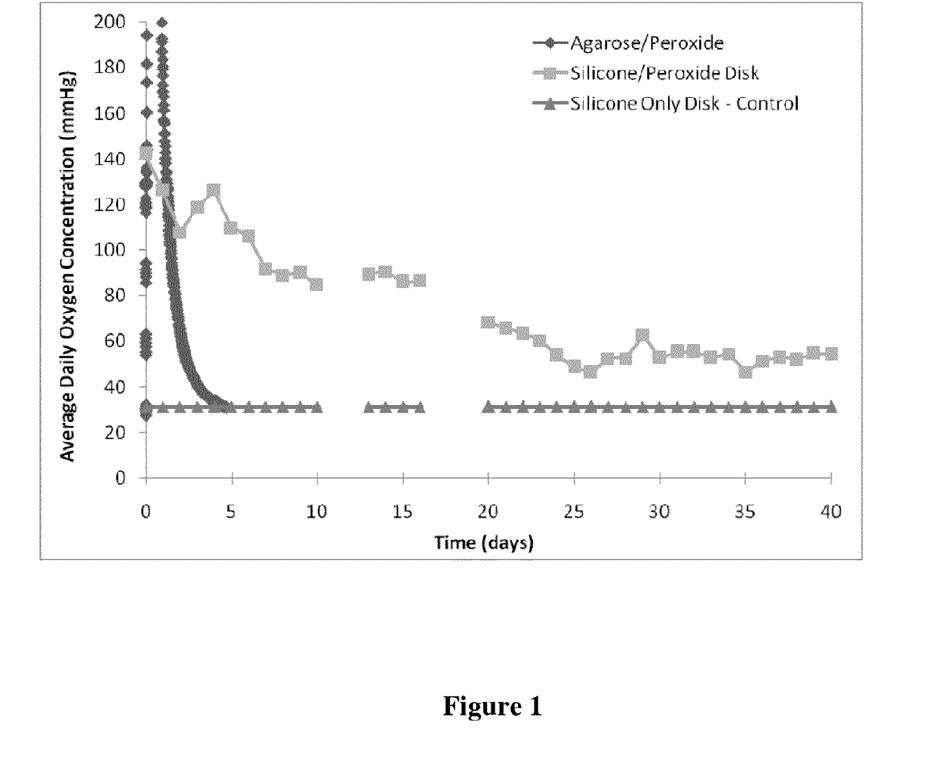
FIG. 1 is a graph showing oxygen sensor readings of saline wells with and without the inventive oxygen-releasing composite and a comparison with an agar-peroxide composite.

Silicone/peroxide disks of variable peroxide concentrations were screened for oxygen generating potential by using oxygen sensors evaluating changes in oxygen generation at low (5%) oxygen tensions. Disks were run over the course of 14 to 45 days and compared to oxygen release in agarose hydrogels. As shown by FIG. 1, oxygen release from the silicone/peroxide composites was steady and sustained over the course of the experiment. In comparison, agarose/peroxide materials had little modulation of peroxide degradation, which resulted in a strong burst of oxygen generation within the first 24 hrs, but a complete loss of oxygen generation after 4 days.

Effects of Silicone/Peroxide Material on Enhancing Cell Viability

Figure 2:
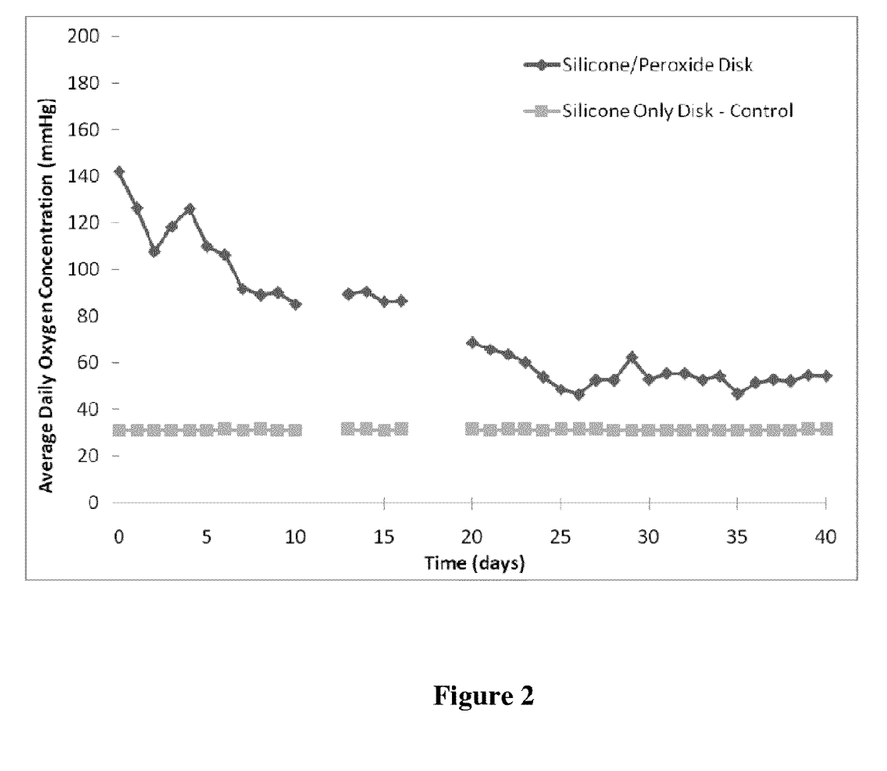
FIG. 2 is a graph showing the number of viable cells in cultures with and without the inventive oxygen-releasing composite.
Figure 3:
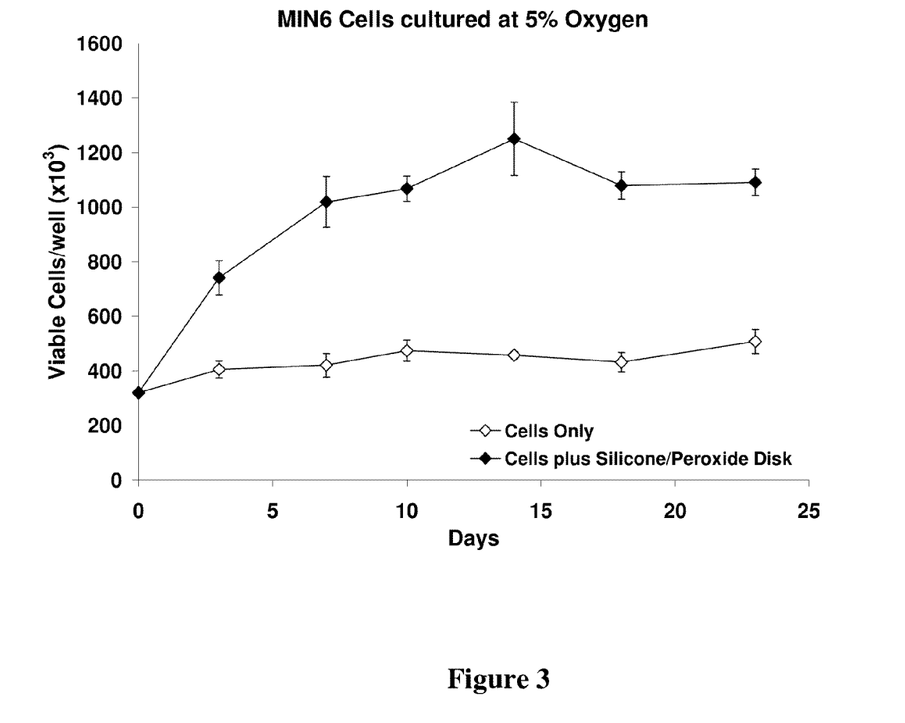
FIG. 3 is a graph showing human islet viability for a variety of oxygen tensions including cultures with and without the inventive oxygen-releasing composite.

The ability of these materials to enhance oxygen levels to a value that results in a sustained and increased level of cell viability was assessed using equilibrated, low initial oxygen (5%) tension saline buffer solutions. As illustrated in FIG. 2, the incubation of MIN6, a beta cell line, using saline buffer solutions with low initial oxygen (5%) tensions with a single 25% w/w peroxide/silicone disk (1 mm thickness/10 mm diameter) resulted in over a 2-fold increase in cell number (assessed via method of transcriptional and translational (MTT) metabolic assay) over the course of 23 days. Experiments using human islets also illustrated significant increases in cell number (see FIG. 3). As FIG. 3 illustrates, islets cultured under low initial oxygen (5%) tensions with a single 25 wt-% peroxide/75 wt-% silicone disk (1 mm thickness/10 mm diameter) exhibited a significant increase in the number of viable cells compared to controls (5%). Of note, islet viability at 5% with the peroxide/silicone composite disks was slightly less than that found for islets exposed to 20% initial oxygen levels.

Figure 4:
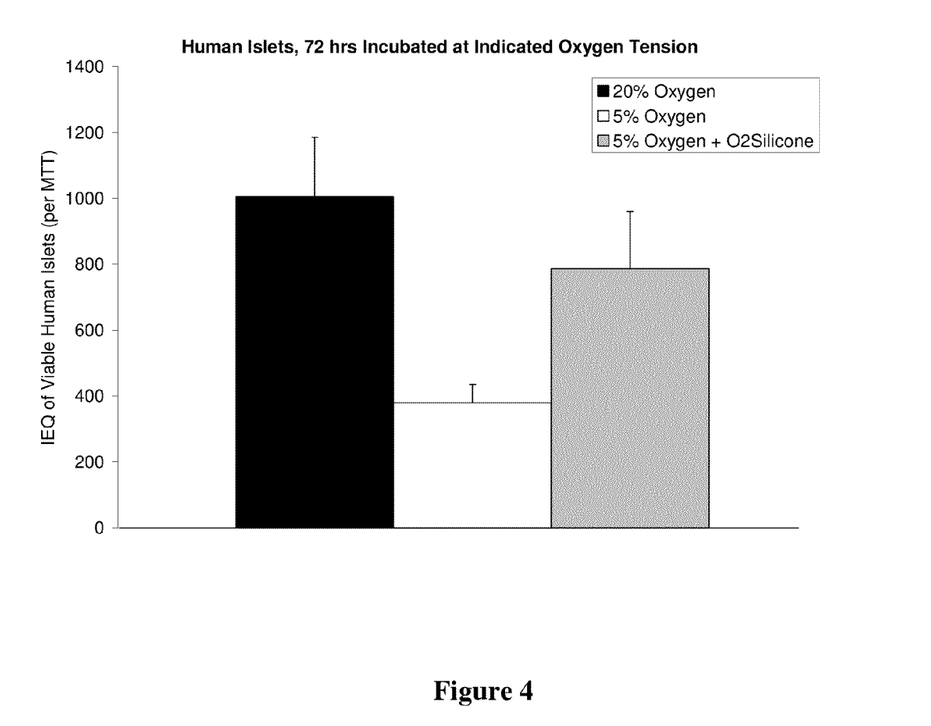
FIG. 4 is a graph showing cell viability following a three day culture in agarose disks with and without the inventive oxygen-releasing composite.

In addition, the capacity to integrate these silicone/peroxide materials within a 3-D gel was also investigated. A single 25 wt-% peroxide/75 wt-% silicone disk (1 mm thickness/10 mm diameter) was loaded within a 3-D agarose gel containing MIN6 cells and the ability of the disk to enhance cell viability was evaluated. As shown in FIG. 4, even within a 3-D agarose gel structure, the oxygen generating material has the capacity to maintain cell viability levels under low initial oxygen tensions (5%) at the same percentage as the 20% initial oxygen tension controls.

Biocompatibility of Silicone/Peroxide Disks in vivo

Assessment of the biocompatibility of silicone/peroxide disks was evaluated via subcutaneous implantation of silicone disks both with and without 25 wt-% peroxide within normal Lewis rats. Disks were removed on Days 30, 60, and 90. Gross evaluation of surrounding tissues at implantation site resulted in no observational differences between silicone and silicone/peroxide disks. Histological assessment was performed via H/E staining. For both silicone and silicone/peroxide disks, minimum cellular adhesion was observed for all of the time points. Cellular adhesion was slightly increased from Day 30 to Day 60 and from Day 60 to Day 90, but no difference between silicone and silicone/peroxide disks was observed. Based on these observations, we find the silicone/peroxide disks to be of comparable biocompatibility and biostability as silicone only disks.

The foregoing description of preferred embodiments of the invention has been presented for the purposes of illustration. The description is not intended to limit the invention to the precise forms disclosed. Indeed, modifications and variations will be readily apparent from the foregoing description. Accordingly, it is intended that the scope of the invention not be limited by the detailed description provided herein.

We claim:

1. A composite for delivering extended-release of oxygen, comprising: a biocompatible polymeric support having a plurality of solid peroxide particles suspended therein, wherein said composite exhibits an oxygen tension value of at least 40 mmHg for a period of at least 14 days.

2. The composite according to claim 1, wherein a weight ratio of biocompatible polymeric support to solid peroxide particles ranges from 1:1 to 99:1.

3. The composite according to claim 1, wherein said siloxysilane-containing polymer comprises a vinyl-containing siloxysilane.

4. The composite according to claim 1, wherein said siloxysilane-containing polymer was formed from a polymer precursor comprising a vinyl-containing, alkyl- or alkylaryl-siloxysilane.

5. The composite according to claim 1, wherein said siloxysilane-containing polymer was formed from at least one polymer precursor selected from the group consisting of:
   3-methacryloyloxypropyltris(trimethylsiloxy)silane,
   3-methacryloyloxypropylpentamethyldisiloxane,
   3-methacryloyloxypropylbis(trimethylsiloxy)methylsilane,
   3-methacryloyloxypropyltris (vinyldimethylsiloxy)silane,
   3-methacryloyloxymethylbis (trimethylsiloxy) (pentamethyldisiloxanyl) silane,
   3-methacryloyloxyethyltris(pentamethyldisiloxanyl)silane, methacryloyloxymethylbis (trimethylsiloxy)methylsilane, methacryloyloxymethyltris(trimethylsiloxy) silane,
   3-methacryloyloxypropylheptacyclopentyl-T8-silsesquioxane,
   3-methacryloyloxypropylheptaisobutyl-T8-silsesquioxane,
   3-acryloyloxypropylmethylbis(trimethylsiloxy)silane,
   3-acryloyloxypropyltris(trimethylsiloxy)silane,
   3-methacryloyloxypropyl-1,1,1, I-triphenyl-3,3-dimethyldisiloxane,
   3-methacrylamidopropyltris(trimethylsiloxy)silane,
   3-acrylamidopropyltris(trimethylsiloxy)silane,
   p-vinylphenyltris(trimethylsiloxy)silane,
   p-vinylbenzyltris(trimethylsiloxy)silane,
   vinyloxyethyltris(trimethylsiloxy)silane,
   vinylnonyldimethyl(trimethylsiloxy) silane,
   vinylnonyltris (trimethylsiloxy) silane,
   vinylmethylbis(trimethylsiloxy)silane,
   vinylpentamethyldisiloxane,
   0-(vinyloxyethy 1)-N-(tris[trimethylsiloxy] silylpropyl1) urethane,
   vinylphenylbis(trimethylsiloxy)silane,
   vinyltris(dimethylsiloxy)silane,
   vinyltris(trimethylsiloxy)silane,
   vinyl-terminated polydimethylsiloxane,
   polydimethylsiloxane mono acrylate,
   polydimethylsiloxane monomethacrylate,
   polymethylphenylsiloxane monoacrylate,
   polymethylphenylsiloxane monomethacrylate,
   3-acryloyloxypropyltris(polydimethylsiloxanyl)silane, and
   a combination thereof.

6. The composite according to claim 1, wherein said siloxysilane-containing polymer was formed from at least one polymer precursor selected from the group consisting of:
   vinyl-terminated polydimethylsiloxane,
   polydimethylsiloxane mono acrylate, and
   polydimethylsiloxane monomethacrylate.

7. The composite according to claim 1, wherein said solid peroxide particles comprise a peroxide selected from the group consisting of calcium peroxide, sodium peroxide, magnesium peroxide, lithium peroxide, potassium peroxide, and combinations thereof.

8. The composite according to claim 1, further comprising a platinum catalyst.

9. The composite according to claim 1, further comprising cellular material coupled to said biocompatible polymeric support.

10. A method of making a composite for delivering extended-release of oxygen according to claim 1, comprising:
    mixing anhydrous polymer precursor solution and a plurality of solid peroxide
    particles until said plurality of solid peroxide particles are suspended therein,
    curing said anhydrous monomer solution with a biocompatible catalyst.

11. The method according to claim 10, wherein said biocompatible catalyst comprises platinum.

12. The method according to claim 10, wherein said biocompatible catalyst is added to said anhydrous polymer precursor solution prior to said mixing step.

13. A method of delivering oxygen to cells, comprising: introducing a composite for delivering extended-release of oxygen according to claim 1 in an aqueous fluid, wherein said composite is in fluid communication with a plurality of cells.

14. The method according to claim 13, wherein said introducing step is in vitro.

15. The method according to claim 13, wherein said introducing step is in vivo.

16. The method according to claim 13, wherein a weight ratio of biocompatible polymeric support to solid peroxide particles ranges from 1:1 to 99:1.

17. The method according to claim 13, wherein said biocompatible polymeric support comprises a siloxysilane-containing polymer.

18. The method according to claim 13, wherein said solid peroxide particles comprise a peroxide selected from the group consisting of calcium peroxide, sodium peroxide, magnesium peroxide, and combinations thereof.

19. The method according to claim 1, wherein said composite exhibits an oxygen tension value of at least 40 mmHg for a period of at least 14-45 days.

\* \* \* \* \*

UNITED STATES PATENT AND TRADEMARK OFFICE
CERTIFICATE OF CORRECTION

PATENT NO. : 8,986,725 B2  
APPLICATION NO. : 13/264140  
DATED : March 24, 2015  
INVENTOR(S) : Stabler et al.

Page 1 of 1

It is certified that error appears in the above-identified patent and that said Letters Patent is hereby corrected as shown below:

In the claims:

Column 10,

Line 11, Claim 5 "3-methacryloyloxypropyl-1,1,1, I-triphenyl-3, 3-dimethyldisiloxane" should read --3-methacryloyloxypropyl-1,1, I-triphenyl-3,3-dimethyldisiloxane--.

Line 22, Claim 5 "0-(vinyloxyethy 1)-N-(tris[trimethylsiloxy] silylpropyl1)urethane" should read --O-(vinyloxyethyl)-N-(tris[trimethylsiloxy] silylpropyl)urethane--.

Signed and Sealed this  
Sixth Day of October, 2015

Michelle K. Lee  
*Director of the United States Patent and Trademark Office*